US011613001B2

(12) United States Patent
Doyle

(10) Patent No.: US 11,613,001 B2
(45) Date of Patent: Mar. 28, 2023

(54) LEG AUGMENTATION SYSTEMS AND METHODS FOR USE

(71) Applicant: LEVITATE TECHNOLOGIES, INC., San Diego, CA (US)

(72) Inventor: Mark C. Doyle, Del Mar, CA (US)

(73) Assignee: LEVITATE TECHNOLOGIES, INC., San Diego, CA (US)

( * ) Notice: Subject to any disclaimer, the term of this patent is extended or adjusted under 35 U.S.C. 154(b) by 517 days.

(21) Appl. No.: 14/667,653

(22) Filed: Mar. 24, 2015

(65) Prior Publication Data

US 2015/0306762 A1    Oct. 29, 2015

Related U.S. Application Data

(60) Provisional application No. 61/969,440, filed on Mar. 24, 2014.

(51) Int. Cl.
*A61F 5/00* (2006.01)
*B25J 9/00* (2006.01)
(Continued)

(52) U.S. Cl.
CPC .............. *B25J 9/0006* (2013.01); *A61F 5/00* (2013.01); *A61F 5/0102* (2013.01); *A61H 3/008* (2013.01); *B25J 9/1045* (2013.01); *B25J 17/00* (2013.01)

(58) Field of Classification Search
CPC .... A61F 5/0102; A61F 5/0193; A61F 5/0585; A61F 5/0125; A61F 5/02; A61F 5/0123;
(Continued)

(56) References Cited

U.S. PATENT DOCUMENTS 1,641,027 A * 8/1927 Feaster .................... A61F 5/02
2/44
2,573,866 A * 11/1951 Murphy ............... A61F 5/0102
602/16
(Continued)

FOREIGN PATENT DOCUMENTS

CN    1838933 A    8/2004
DE    19652416 A1    6/1998
(Continued)

OTHER PUBLICATIONS

European Patent Office, Search Report for Corresponding European Application No. 15768384.8-1018, dated Feb. 21, 2018, 10 pages.
(Continued)

*Primary Examiner* — Adam Baker
(74) *Attorney, Agent, or Firm* — William A. English; Vista IP Law Group LLP

(57) ABSTRACT

Systems and methods are provided for supporting one or both legs of a user using a harness configured to be worn on a body of a user; and a leg support coupled to the harness configured to support a leg of the user, the leg support configured to accommodate movement of the leg while following the movement without substantially interfering with the movement of the user's arm. One or more compensation elements may be coupled to the leg support to apply an offset force to at least partially offset a gravitational force acting on the leg as the user moves and the leg support follows the movement of the user's leg, the one or more compensation elements providing a force profile that varies the offset force based on an orientation of the leg support.

19 Claims, 10 Drawing Sheets

(51) Int. Cl.
  *B25J 9/10* (2006.01)
  *A61F 5/01* (2006.01)
  *A61H 3/00* (2006.01)
  *B25J 17/00* (2006.01)
(58) Field of Classification Search
  CPC ...... A61F 2005/0179; A61F 2005/0181; A61F 2005/0183; A61F 2005/0146; A61F 2005/0151; A61F 2005/0135; A61F 2005/0155; A61F 2005/0165; A61F 2005/0169; A61F 2005/0148; A61F 2005/0153; A61H 1/02; A61H 1/0247; A61H 1/0255; A61H 1/0262; B25J 9/0015; B25J 9/0078
  USPC ........................ 602/19, 12, 16, 5, 20, 21, 23
  See application file for complete search history.

(56) References Cited

U.S. PATENT DOCUMENTS

| | | | | |
|---|---|---|---|---|
| 2,772,674 | A * | 12/1956 | Swiech | A61F 5/0102 602/23 |
| 4,456,003 | A * | 6/1984 | Allard | A61F 5/0102 602/16 |
| 5,058,574 | A * | 10/1991 | Anderson | A61F 5/0125 602/16 |
| 5,111,983 | A | 5/1992 | Simmons et al. | |
| 2002/0110793 | A1 * | 8/2002 | Eastwood | A63B 23/04 434/253 |
| 2006/0206043 | A1 * | 9/2006 | Yakimovich | A61F 5/0125 602/16 |
| 2008/0161738 | A1 | 7/2008 | Giesen | |
| 2008/0161937 | A1 | 7/2008 | Sankai | |
| 2010/0094185 | A1 * | 4/2010 | Amundson | A61F 5/0102 602/16 |
| 2010/0271051 | A1 | 10/2010 | Sankai et al. | |
| 2011/0040216 | A1 | 2/2011 | Herr et al. | |
| 2011/0127390 | A1 | 6/2011 | Brown | |
| 2011/0251534 | A1 | 10/2011 | Matsuoka | |
| 2012/0089065 | A1 * | 4/2012 | Pflaster | A61B 5/1071 602/16 |
| 2012/0184880 | A1 | 7/2012 | Doyle | |
| 2012/0271207 | A1 * | 10/2012 | Schoen | A61F 5/0102 601/34 |
| 2013/0131560 | A1 | 5/2013 | Ferguson et al. | |
| 2014/0158839 | A1 | 6/2014 | Doyle | |
| 2015/0016923 | A1 * | 1/2015 | Brown | A61F 5/01 414/1 |
| 2015/0119777 | A1 * | 4/2015 | Garrish | A61F 5/0123 602/16 |

FOREIGN PATENT DOCUMENTS

| | | |
|---|---|---|
| DE | 202009000076 | 5/2010 |
| GB | 2472036 B | 12/2013 |
| JP | 10071161 A | 3/1998 |
| JP | 2002153115 A | 5/2002 |
| JP | 2003144467 | 5/2003 |
| JP | 2003220102 | 8/2003 |
| JP | 2005177420 | 7/2005 |
| JP | 2006305225 | 11/2006 |
| JP | 2009273711 A | 5/2008 |
| JP | 2008295696 A | 12/2008 |
| JP | 2010110543 | 5/2010 |
| JP | 2010142353 | 7/2010 |
| JP | 2012090849 | 5/2012 |
| JP | 2012200828 | 10/2012 |
| WO | 2009029693 A1 | 3/2009 |
| WO | 2010019300 A1 | 2/2010 |
| WO | 2010025409 A1 | 3/2010 |
| WO | 2013106532 A1 | 7/2013 |
| WO | 2013155065 A1 | 10/2013 |

OTHER PUBLICATIONS

Korean Intellectual Property Office, International Search Report for corresponding International Application No. PCT/US2015/022339, dated Jun. 24, 2015, 4 pages.
Korean Intellectual Property Office, Written Opinion for corresponding International Application No. PCT/US2015/022339, dated Jun. 24, 2015, 15 pages.
European Patent Office, Search Report for Corresponding European Application No. 15768384.8-1018, dated Feb. 1, 2019, and Response filed, dated Jun. 6, 2019, 10 pages.
Japan Patent Office, Notice of Rejection for Corresponding Japanese Application No. 2016-558598, dated Jul. 24, 2019, and translation, 12 pages.
European Patent Office, Search Report for Corresponding European Application No. 15768384.8-1016, dated Jan. 16, 2020, 7 pages.
Japan Patent Office, Notice of Rejection and translation for Corresponding Japanese Application No. 2016-558598, dated Mar. 11, 2020, 33 pages.
European Patent Office Examining Division, Examination Report n the Corresponding International Application, EP Application No. 15 768 384.8, dated Nov. 25, 2020, 7 pages.
Dan, Yoshitaka, Patent Examiner, Japanese Patent Office, Notice of Rejection for corresponding Japanese Patent Application No. 2016-558598, dated Sep. 25, 2020, 20 pages.

* cited by examiner

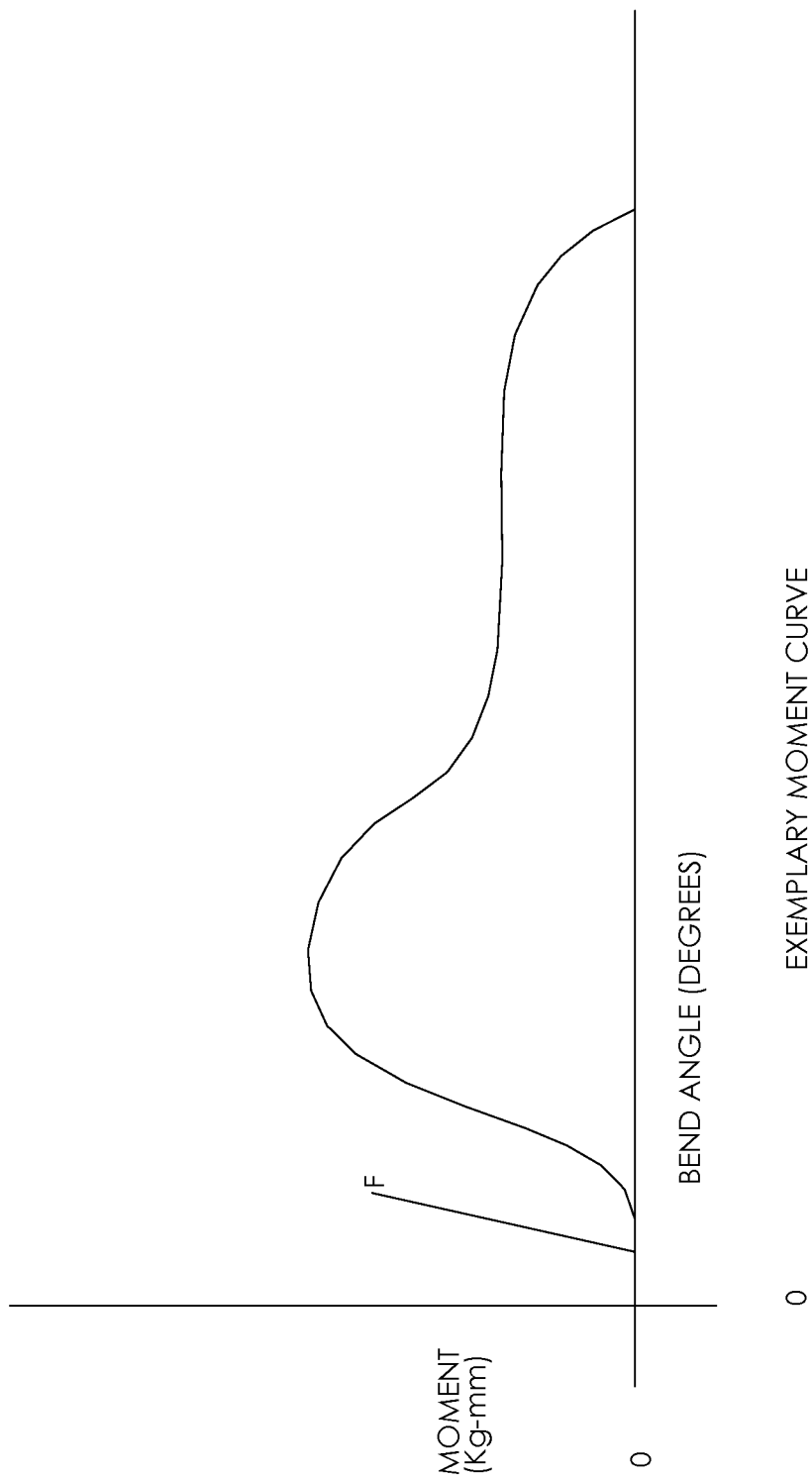

LEG AUGMENTATION SYSTEMS AND METHODS FOR USE

RELATED APPLICATION DATA

The present application claims benefit of provisional application Ser. No. 61/969,440, filed Mar. 24, 2014, the entire disclosure of which is expressly incorporated by reference herein.

FIELD OF THE INVENTION

The present invention relates to systems and methods that enhances the function of the user's leg muscles, and more particularly to spring-loaded leg augmentation systems that enhance the function of the user's leg muscles and/or support, stabilize, and/or unload various joints of the user's skeleton.

BACKGROUND

Many tasks require repetitive bending of the legs, often with heavy loads, which can result in muscle fatigue and injury to joints such as the hip and knee. Persons with injuries, arthritis, or other disabilities may have difficulty in performing everyday tasks involving the legs, such as walking, rising from a chair or a kneeling position, crouching, or lifting light loads. Aging joints can be irritated and damaged by everyday activities. Persons in rehabilitation may need stabilization of injured joints.

Thus, there is a need for support systems that may relieve fatigue and/or reduce injury experienced by persons performing tasks involving moderate to large ranges of motion of their legs.

SUMMARY

The present invention is directed to systems and methods that enhance the function of the user's leg muscles. More particularly, the present invention is directed to spring-loaded leg augmentation systems that enhance function of the user's leg muscles and/or that support, stabilize, and/or unload various joints of the user's skeleton.

In an exemplary embodiment, a system is provided for supporting a user's leg that includes a harness configured to be worn on a body of a user; a leg support coupled to the harness configured to support a leg of the user, the leg support configured to accommodate movement of the leg while following the movement without substantially interfering with the movement of the leg; and one or more compensation elements coupled to the leg support to apply an offset force to at least partially offset a gravitational force acting on the leg as the user moves and the leg support follows the movement of the leg. In an exemplary embodiment, the one or more compensation elements are configured to provide a force profile that varies the offset force based on an orientation of the leg support, e.g., including a resilient element and one or more pulleys mounted on the leg support.

In accordance with another embodiment, a system is provided for supporting a leg of a user that includes a harness comprising an attachment band configured to be worn on around a waist or hops of a user; a hip strut comprising a first end coupled to the attachment band and a second end configured to be disposed adjacent the user's hip or thigh; a leg support comprising a leg bracket pivotally coupled to the second end of the hip strut such that the leg bracket is pivotable about to accommodate movement of the user's leg while following the movement without substantially interfering with the movement of the user's leg; and one or more compensation elements mounted on the leg bracket to at least partially offset a gravitational force acting on the user's leg as the user moves and the leg bracket follows the movement of the user's leg.

In accordance with still another embodiment, a system is provided for supporting a leg of a user that includes a harness comprising an attachment band configured to be worn on around a waist or hops of a user; a hip strut comprising a first end coupled to the attachment band and a second end configured to be disposed adjacent the user's hip or thigh; a first leg support comprising a first leg bracket pivotally coupled to the second end of the hip strut and a first leg strap for securing the first leg bracket to a user's thigh such that the first leg bracket is pivotable about to accommodate movement of the user's leg while following the movement without substantially interfering with the movement of the user's leg; a lower leg strut comprising a first end coupled to the first leg bracket and a second end configured to be disposed adjacent the user's thigh or knee; a second leg support comprising a second leg bracket pivotally coupled to the second end of the hip strut and a second leg strap for securing the first leg bracket to a user's calf such that the second leg bracket is pivotable about to accommodate movement of the user's leg while following the movement without substantially interfering with the movement of the user's leg; and one or more compensation elements mounted on the first and second leg brackets to at least partially offset a gravitational force acting on the user's leg as the user moves and the first and second leg brackets follow the movement of the user's leg.

In accordance with yet another embodiment, a method is provided for supporting a leg of a user during one or more tasks that includes placing a harness on the user; supporting a portion of the user's leg using a leg support such that the leg support subsequently follows movement of the user's leg; and performing one or more tasks involving movement of the user's leg, the leg support comprising one or more compensation elements that apply an offset force to at least partially offset a gravitational force acting on the leg as the user moves without substantially interfering in the movement.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 3B shows another exemplary moment/angle relationship curve with dwell.

DETAILED DESCRIPTION OF THE EXEMPLARY EMBODIMENTS

Figure 1A:
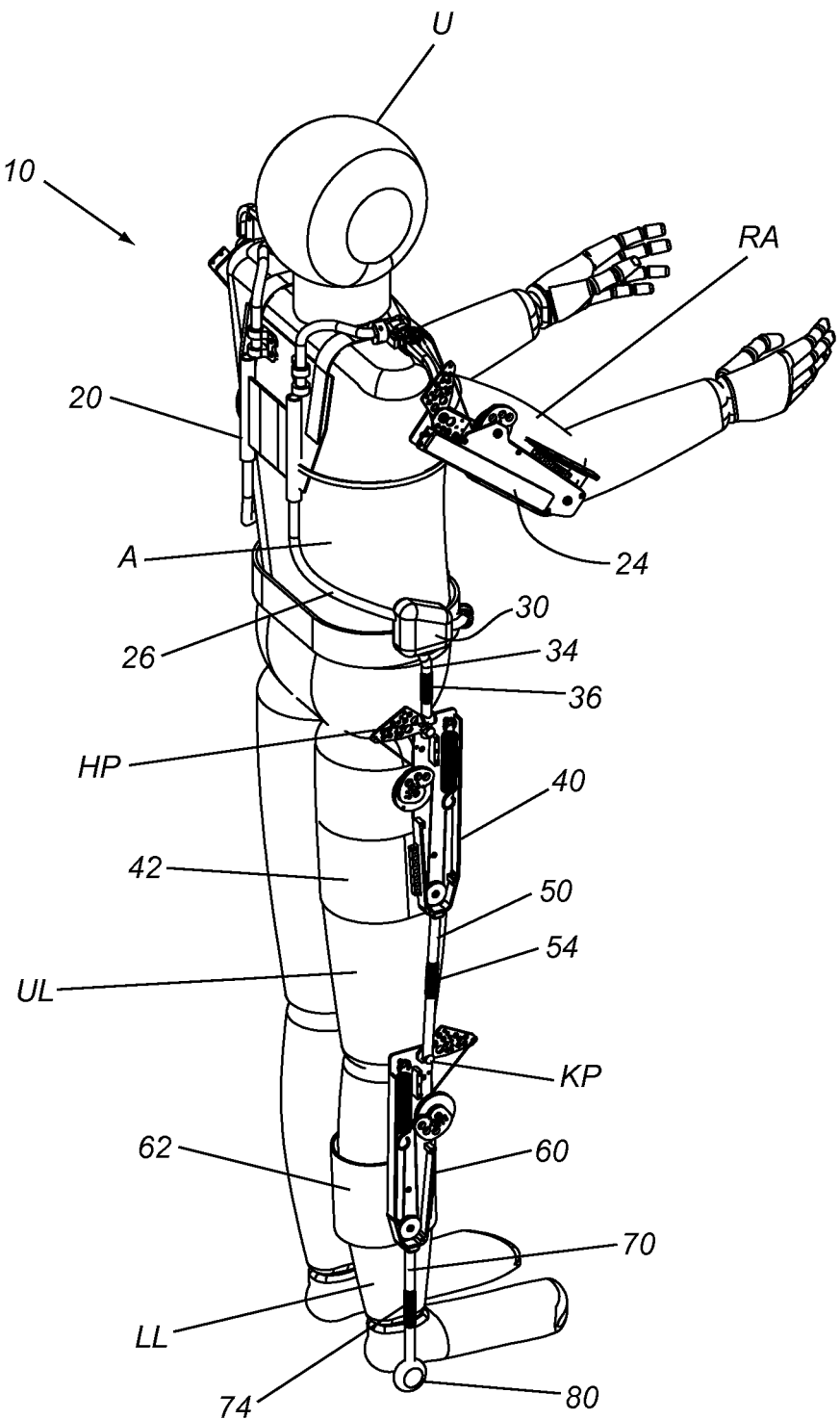
FIG. 1A is a rear perspective view of an exemplary embodiment of a leg augmentation system worn by a user in a rest position.
Figure 1B:
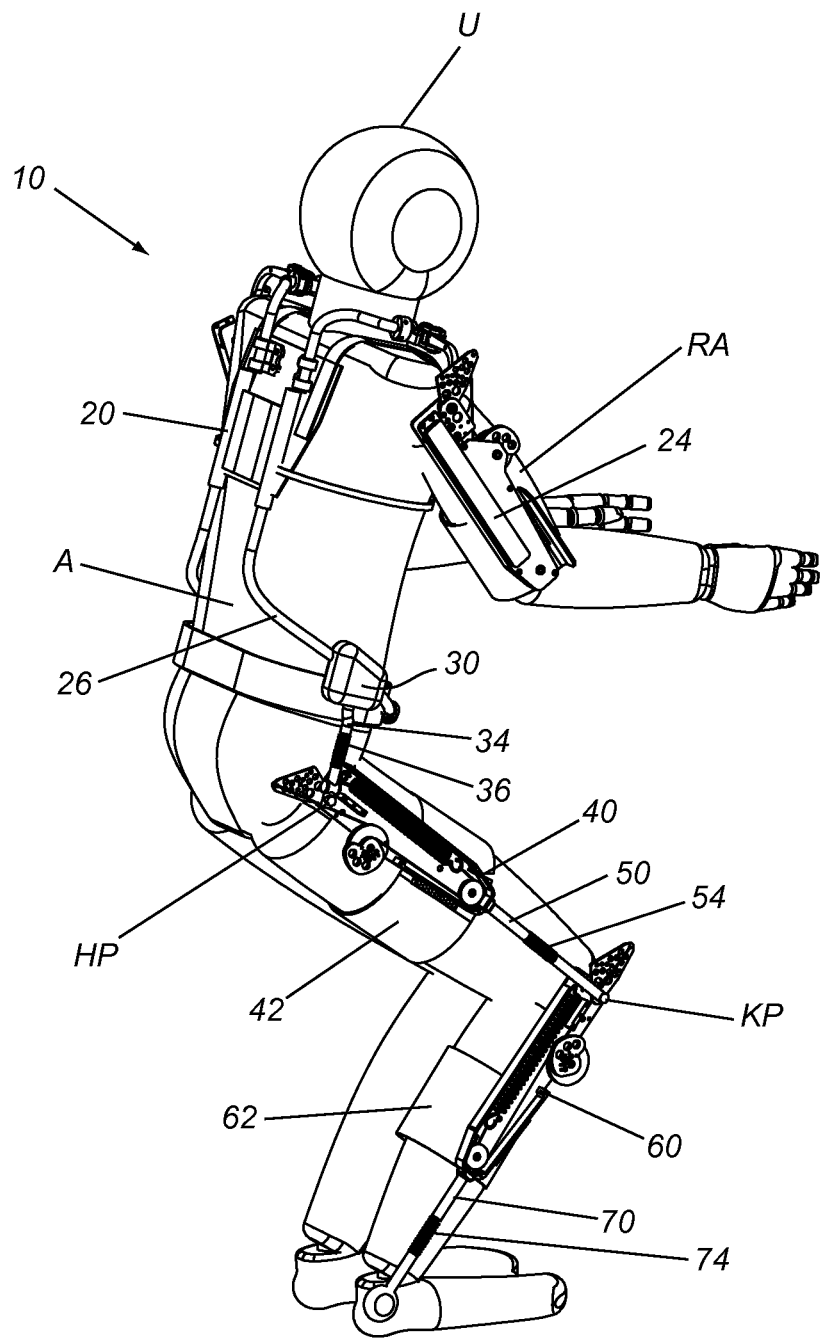
FIG. 1B is a rear perspective view of the leg augmentation system of FIG. 1A in a loaded position.

Turning to the drawings, FIGS. 1A and 1B show an exemplary embodiment of a leg augmentation system 10 that may be worn by a user U. FIG. 1A is a rear perspective view of the leg augmentation system 10 in a rest position, e.g., in which the system 10 applies substantially no support forces to a user's body U.

In the example shown, the user U is also wearing an adaptive arm support system 20 on their abdomen A. Exemplary arm support systems and/or harnesses that may be included in the system 10 are disclosed in Ser. No. 13/353,268, filed Jan. 18, 2012 (and published as U.S. Publication No. 2012/0184880), Ser. No. 13/563,728, filed Jul. 31, 2012 (and published as U.S. Publication No. 2014/0033391), and Ser. No. 14/102,466, filed Dec. 10, 2013 (and published as U.S. Publication No. 2014/0158839). The entire disclosures of these applications are expressly incorporated by reference herein.

In the example shown, an arm support assembly 24 supports the user's right arm RA. Attached to the adaptive arm support 20, for example, on abdomen tube 26, is a connection element 30. The connection element 30 may permit hip strut 34 to be joined to the adaptive arm support system 20, and may be rigid, articulating, flexible, multi-axial, quick-disconnecting, or have other convenient functional characteristics for joining portions of the system together and/or separating them, as desired. The hip strut 34 joins hip cassette 40 at its upper edge. The hip strut 34 may contain optional axial elastic element 36 (e.g., a guided compression spring within a housing, not shown), which may provide an axial separating force between the connection element 30 and hip cassette 40.

The hip cassette 40 may function similarly to the arm support assembly 24 in that it may employ one or more cables, pulleys (symmetric and/or asymmetric), and/or springs to provide a position-dependent restoring force to a limb (in this case the user's upper leg UL), e.g., such as the exemplary configurations disclosed in the applications incorporated by reference herein.

Generally, the hip cassette 40 includes a leg bracket secured to the user's leg that carries a pulley/cable arrangement to manage forces, e.g., similar to compound bows used in archery. In an exemplary embodiment, a dual path pulley is pivotally joined to the leg bracket at a location offset from a hip pivot point HP along the leg bracket. The dual path pulley may have an integral spring cable pulley and integral cam cable pulley fixed relative to one another. The spring cable pulley may have a substantially circular shape around pivot, while the cam cable pulley may have an asymmetrical shape around the pivot, e.g., including a lobe that is further from the pivot than the perimeter of the spring cable pulley.

A spring cable has a first end joined to one end of a spring or other resilient element (with the other end of the resilient element attached to the leg bracket), and a second end coupled to the spring cable pulley at an attachment point. A cam cable has a first end joined to the cam cable pulley at an attachment point, and a second end joined to the leg bracket.

The hip cassette 40 may pivot about the hip pivot point HP, which may be located on axis with the user's hip. An upper leg strap 42 or other fastener may secure the hip cassette to the user's upper leg UL. In the rest position shown in FIG. 1A, the hip cassette 40 may be applying substantially no restoring force to the user's upper leg UL, and the spring may be relatively retracted.

A lower leg strut 50 joins the hip cassette 40 at its lower end, and attaches to knee cassette 60 at (or near) knee pivot KP, which may be located on axis with the user's knee. Lower leg strut 50 may contain optional axial elastic element 54 (e.g., a guided compression spring), which may provide an axial separating force between the hip cassette 40 and knee pivot KP. The knee cassette 60 may function similarly to the hop cassette 40 and/or the arm support assembly 24 in that it may employ one or more cables, pulleys (symmetric and/or asymmetric), and/or springs to provide a position-dependent restoring force to a limb (in this case the user's lower leg LL), also similar to the configurations disclosed in the applications incorporated by reference herein.

A lower leg strap or other fastener 62 may secure the knee cassette 60 to the user's lower leg LL. In the rest position shown in FIG. 1A, the knee cassette 60 may be applying substantially no restoring force to the user's lower leg LL, and the spring may be relatively retracted.

A lower leg strut 70 may join the knee cassette 60 at its lower end, and may contain optional axial elastic element 74 (e.g., a guided compression spring), which may provide an axial separating force between the knee cassette 60 and the ground or other contact surface under the user U. Optionally, a termination element 80 may be located at the end of the lower leg strut 70, and may include one or more of a roller, pad, foot, or other structure. By terminating at the ground, the leg augmentation system 10 may also serve to "unload" the joints of the leg and back of the user U, e.g., allowing the weight of the upper limbs, torso, and/or any equipment or cargo (not shown) carried by the user U to be transferred to the ground through the system of struts and cassettes.

FIG. 1B is a rear perspective view of the leg augmentation system 10 in a loaded position, e.g., consistent with the user U crouching, for example, to lift a heavy load (not shown). As shown, the hip cassette 40 has pivoted about the hip pivot point HP, and the knee cassette 60 has pivoted about the knee pivot point KP. In the loaded position shown in FIG. 1B, the cassettes 40, 60 may apply a restoring force to the user's leg, and the springs may be relatively extended.

Figure 2A:
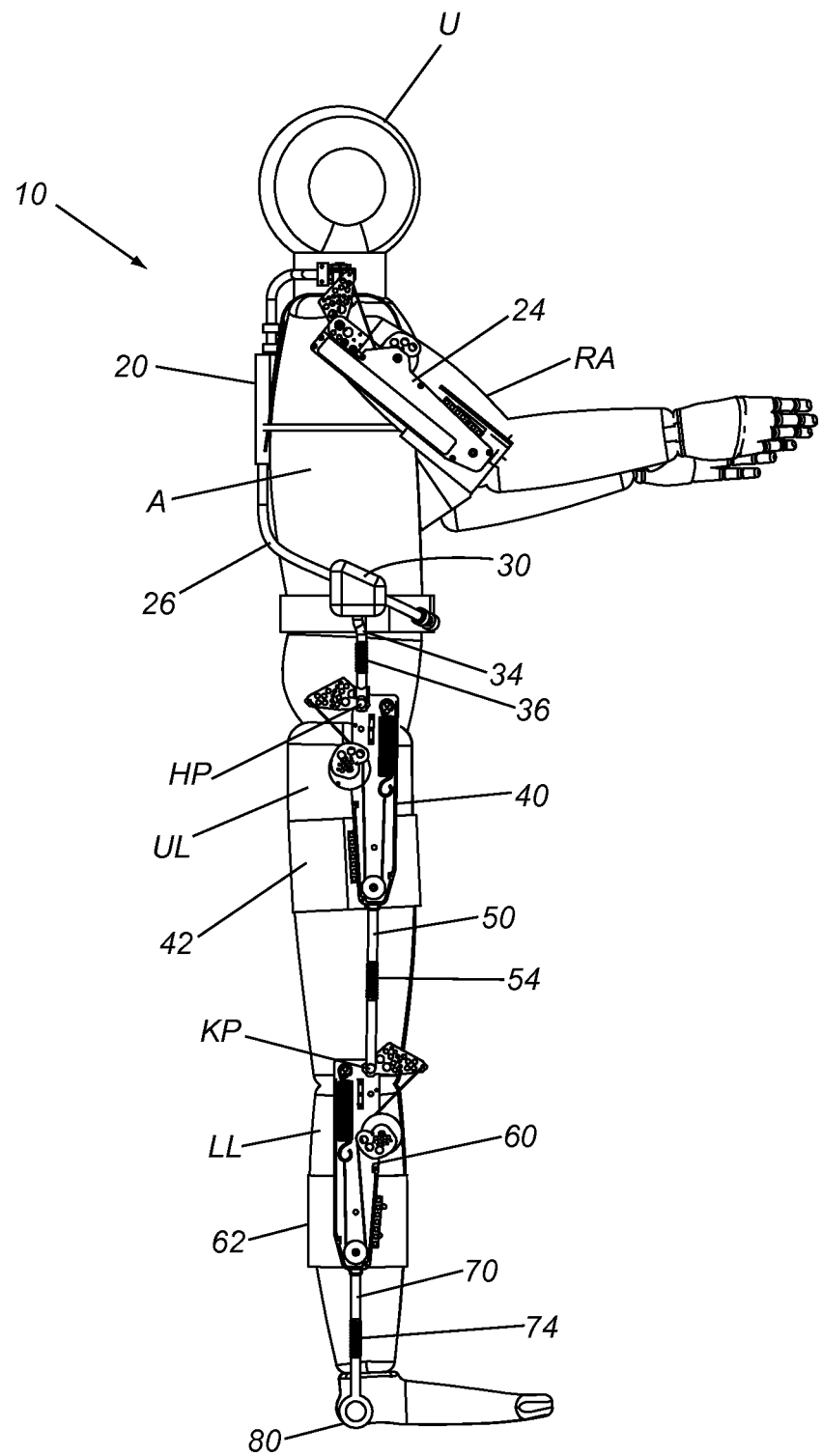
FIG. 2A is a side view of the leg augmentation system of FIGS. 1A and 1B in the rest position.

FIG. 2A is a side view of the leg augmentation system 10 in the rest position. As discussed with reference to FIGS. 1A and 1B, the hip cassette 40 and knee cassette 60 may be applying substantially no restoring force to the user's upper and lower leg.

Figure 2B:
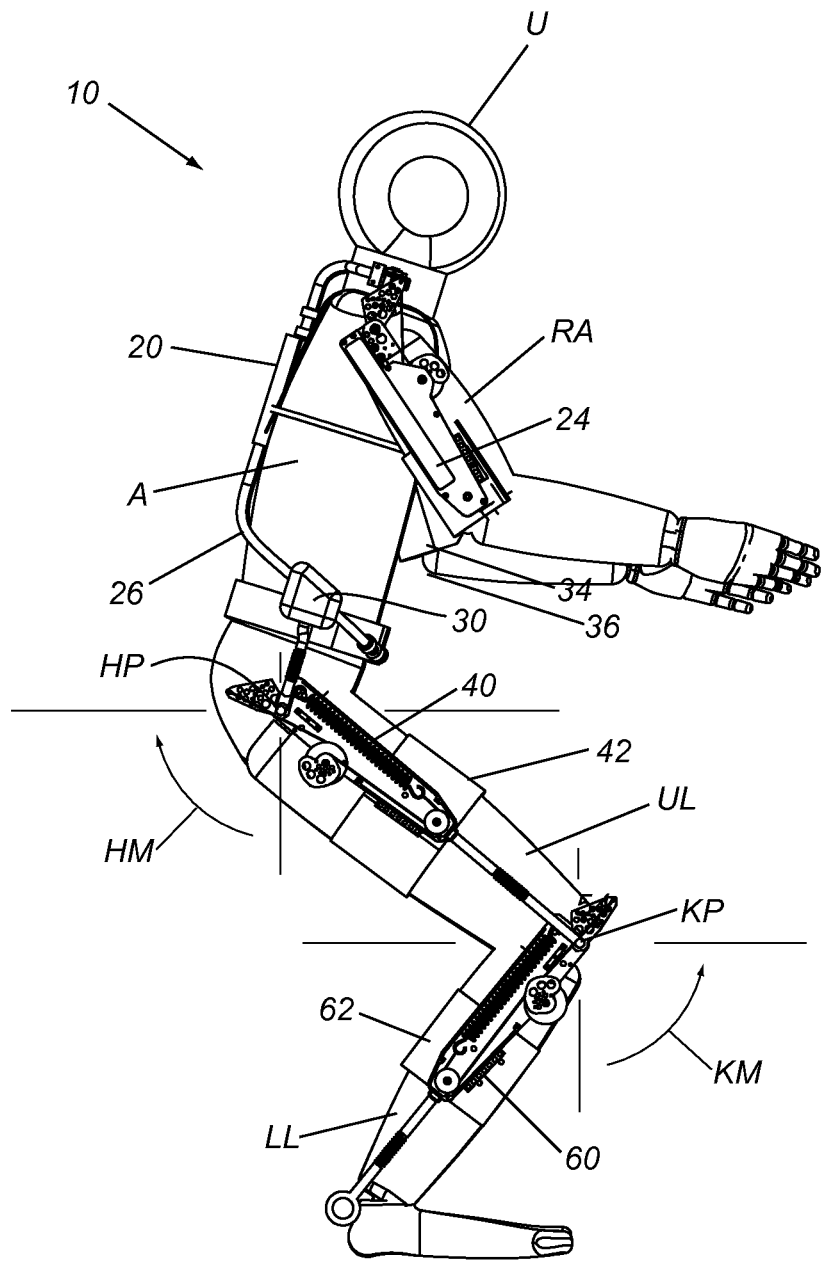
FIG. 2B is a side view of the leg augmentation system of FIGS. 1A and 1B in the loaded position.

FIG. 2B is a side view of the leg augmentation system 10 in the loaded position. As shown, the hip cassette 40 has pivoted about the hip pivot point HP, and the knee cassette 60 has pivoted about the knee pivot point KP. In such loaded position, the two cassettes 40, 60 may apply restoring forces based on the characteristics of their geometries, pulleys, and/or springs. For example, the hip cassette 40 may be applying a restoring force or moment HM about the hip pivot HP, and the knee cassette 60 may be applying a restoring force or moment KM about the knee pivot KP. These restoring forces may aid the user U in returning to an upright position, such as that shown in FIG. 2A.

Figure 3A:
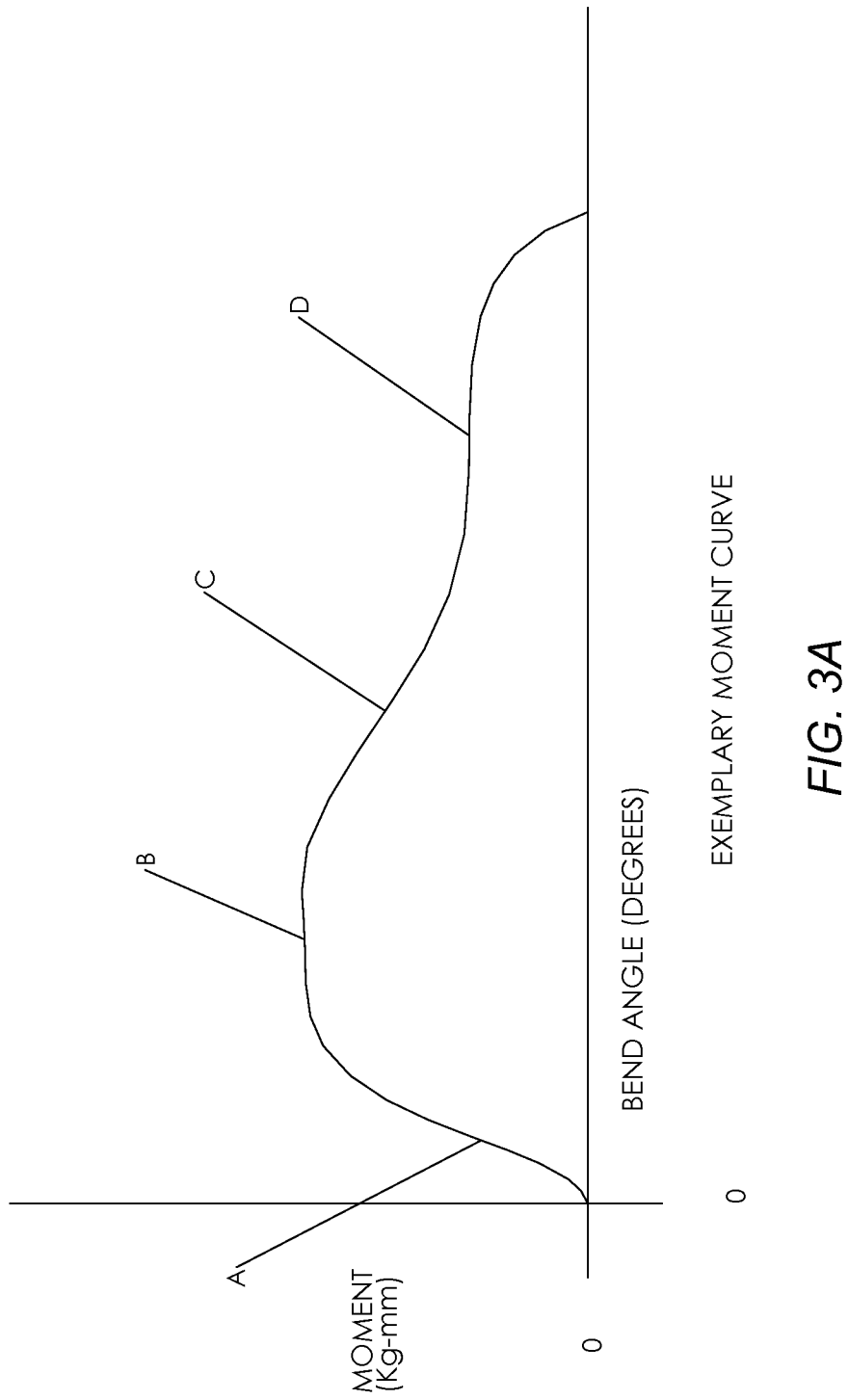
FIG. 3A shows an exemplary moment/angle relationship curve that may be applied to the user's legs during use of a leg augmentation system, such as that shown in FIGS. 1A-2B.

To further illustrate the restoring forces, FIG. 3A shows an exemplary position/moment relationship curve that may be generated by the cassettes 40 or 60. In response to the angle of bend of the upper leg UL relative to the user's abdomen, or the angle of bend of the lower leg LL relative to the upper leg UL, the restoring moment may increase or decrease according to the needs of the user U. The shape of the curve is determined by the geometry of the system 10, i.e., the cassettes 50, 40, and the pulleys within the cassettes 40, 60. For example, as the user U bends at the hip, the restoring moment applied by the system 10 may increase (region "A"). As the user U rotates the hip further, a relatively consistent restoring moment may be applied (region "B"). If desired, the restoring moment may decrease with increasing rotation of the hip joint (region "C"), and then may dwell at a consistent level (region "D") before returning to zero.

FIG. 3B shows another exemplary position/moment relationship curve with a dwell (region "F") in which no restoring moment is applied to the limb. This may be consistent with actions such as walking, in which a restoring force may be undesirable within a certain initial range of motion of the limb. Once the limb is rotated sufficiently to require a restoring moment, the moment may increase as needed. Like the curve shown in FIG. 3A, the shape of the curve may be varied as desired for the intended application. The characteristics of the cassettes 40, 60 may be configured to aid in lifting, walking, siting, rising, rehabilitation of injured or arthritic joints, and/or for many other purposes.

Figure 4A:
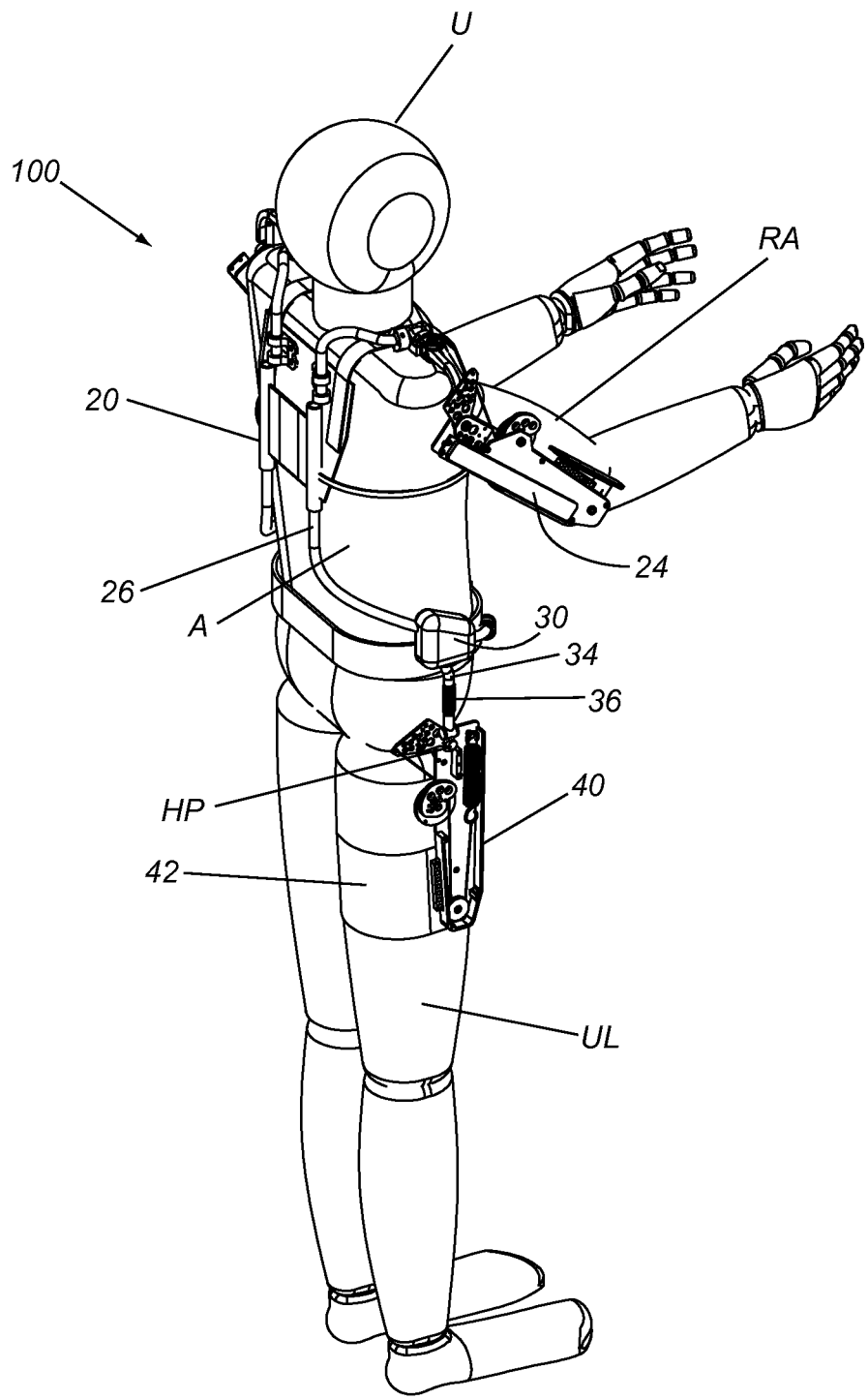
FIG. 4A is a rear perspective view of an exemplary embodiment of an upper leg augmentation system worn by a user in a rest position.

Turning to FIG. 4A, an exemplary embodiment of an upper leg augmentation system 100 is shown in a rest position. Similar to the leg augmentation system 10 of FIGS. 1-3, the upper leg augmentation system 100 includes a hip cassette 40, disposed to apply a restoring moment to the user's upper leg UL, but, unlike the system 10, does not include a knee cassette.

Figure 4B:
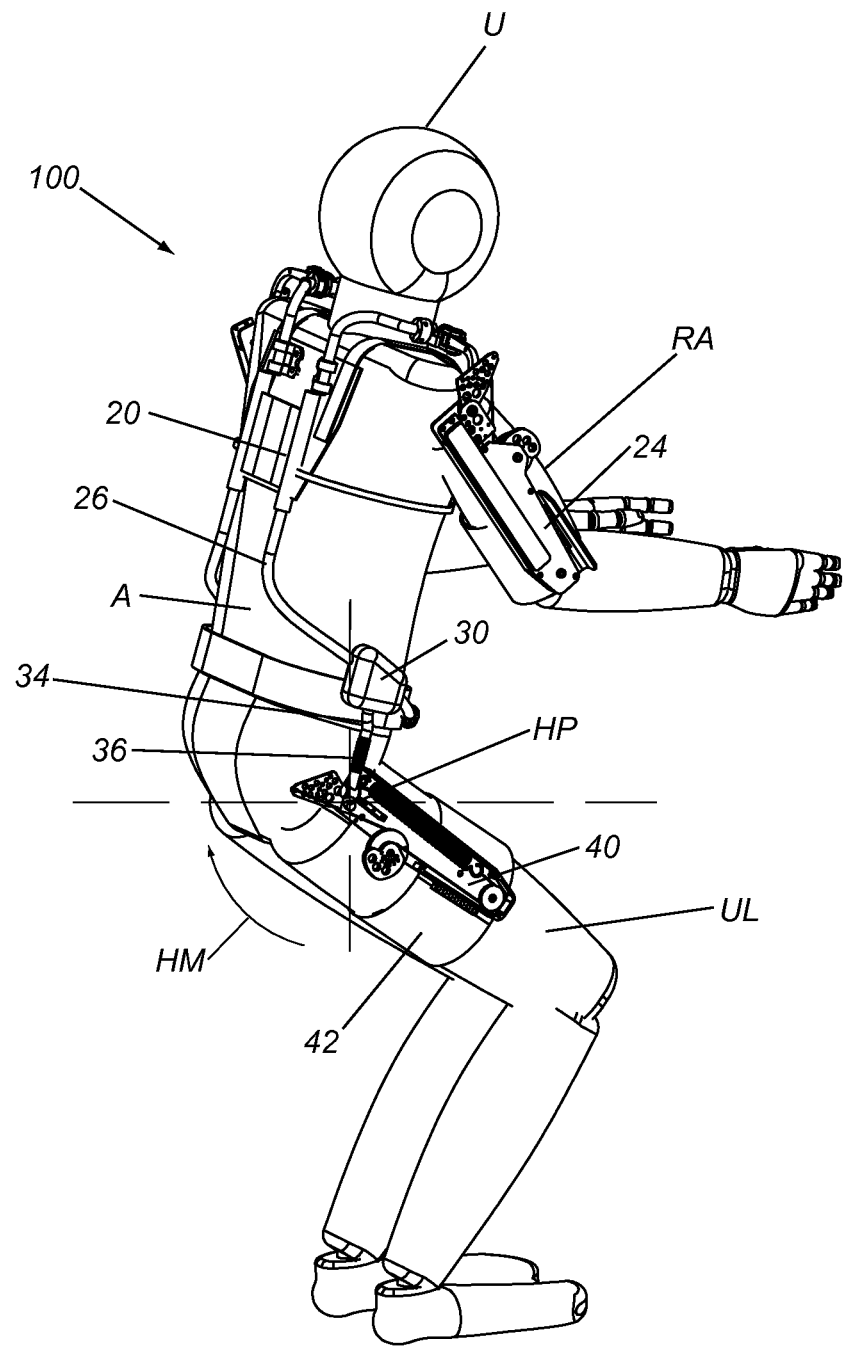
FIG. 4B is a rear perspective view of the upper leg augmentation system of FIG. 4A in a loaded position.

FIG. 4B shows the upper leg augmentation system 100 of FIG. 4A in A loaded position. As shown, the hip cassette 40 has pivoted about hip pivot point HP, and is applying a restoring force or moment HM about hip pivot HP, e.g., similar to the system 10.

Figure 5A:
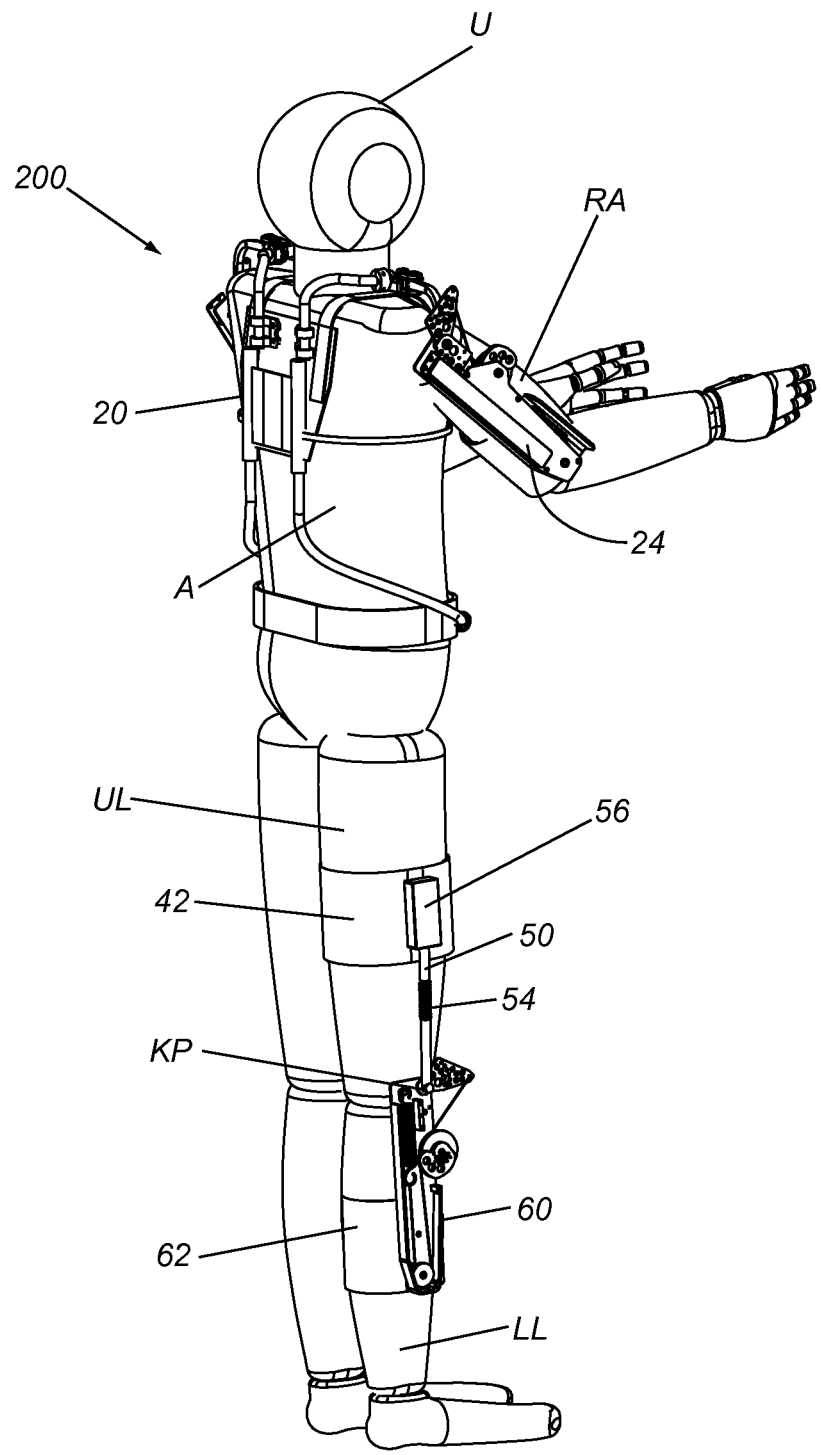
FIG. 5A is a rear perspective view of an exemplary embodiment of a lower leg augmentation system worn by a user in a rest position.

FIG. 5A shows an exemplary embodiment of a lower leg augmentation system 200 in a rest position. Similar to the leg augmentation system 10 of FIGS. 1-3, the lower leg augmentation system 200 includes a knee cassette 60, disposed to apply a restoring moment to the user's lower leg LL, but, unlike the system 10, does not include a hip cassette.

Figure 5B:
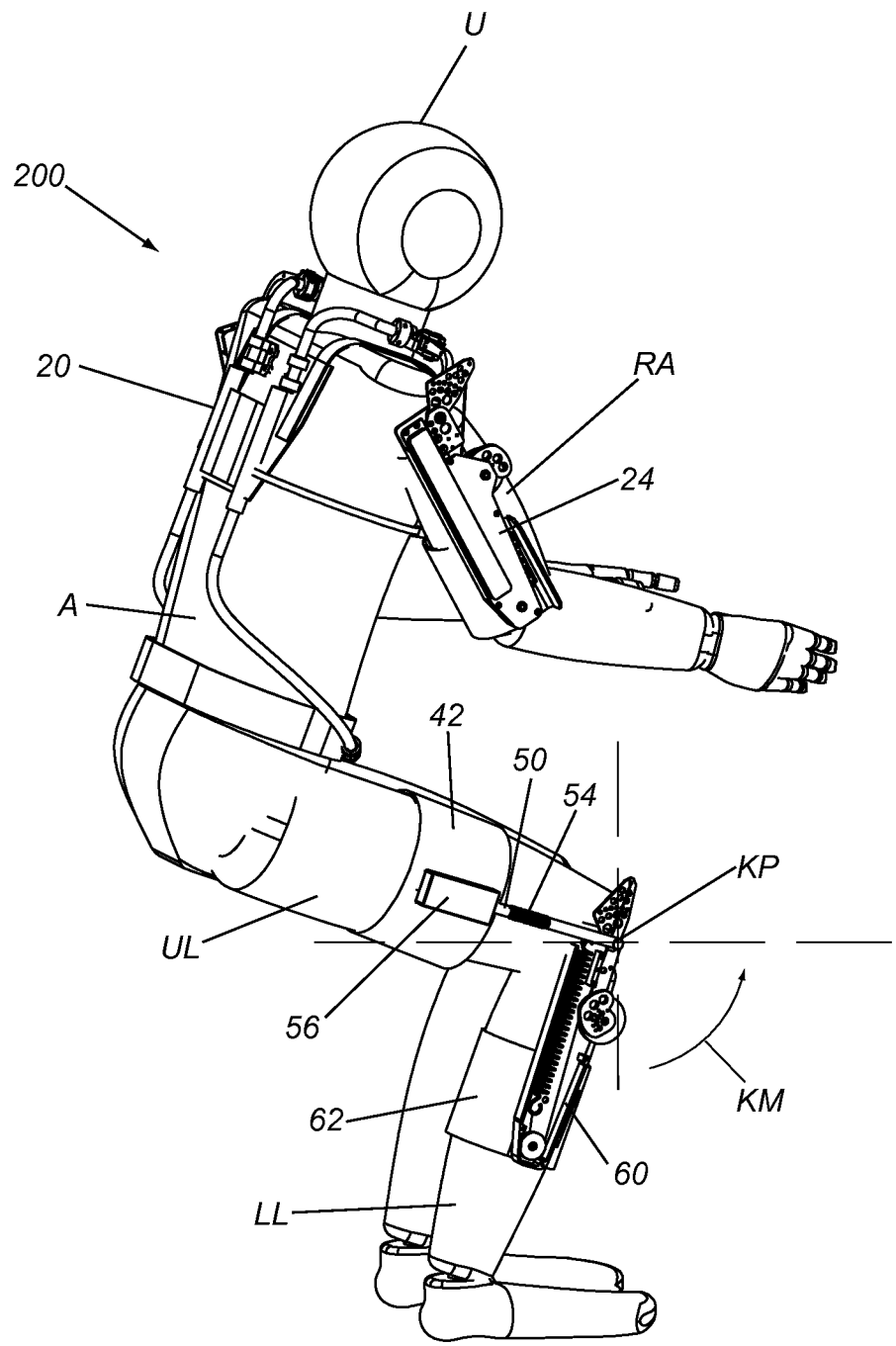
FIG. 5B is a rear perspective view of the lower leg augmentation system of FIG. 5A in a loaded position.

FIG. 5B shows the lower leg augmentation system 200 in a loaded position. As shown, the knee cassette 60 has pivoted about knee pivot point KP, and is applying a restoring force or moment KM about knee pivot KP.

Generally, the devices and systems herein may be worn or otherwise placed on the user's body, e.g., by securing a harness onto one or both of the user's legs, and/or abdomen, e.g., their waist, hips, shoulders, back, chest, and the like. One or more leg supports of the devices or systems, e.g., coupled to or otherwise carried by the harness, may be used to support the user's leg(s) such that the leg support(s) subsequently follows movement of the user's leg(s). The user may then perform one or more tasks involving movement of the user's leg(s), e.g., bending, walking, turning, and the like with the leg support(s) at least partially offsetting a gravitational force acting on the user's leg(s) and/or at least partially transferring the gravitational force from the joints to other locations on the leg(s) and/or to the user's abdomen (or other structures) during the movement without substantially interfering in the movement. Thus, the devices and systems herein may facilitate the user performing the task(s) for greater lengths of time and/or with reduced fatigue and/or injury. In addition or alternatively, other benefits may be realized, including reduced strain on one or more of the user's knees, ankles, hips, back and spine and/or improved leg stability by the user.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for supporting a leg of a user, comprising:
a harness configured to be worn on a body of a user;
a leg support coupled to the harness configured to support a leg of the user, the leg support comprising one or more joints configured to accommodate bending of the leg while following the bending; and
a spring mechanism coupled to the leg support to apply an offset force to the leg support to at least partially offset a gravitational force acting on the body as the user bends the leg and the leg support follows the bending of the leg,
wherein the leg support comprises a hip pivot joint fixedly coupled relative to the harness and a leg bracket pivotally coupled to the hip pivot such that the leg bracket is pivotable in a first direction about the hip pivot joint as the user crouches or leans forward from an upright position and bends the user's upper leg relative to the user's hip and the spring mechanism applies an offset force to the leg bracket in a second direction opposite to the first direction to at least partially offset a gravitational force acting on the body and return the user towards the upright position, wherein the spring mechanism comprises a spring mounted on the leg bracket, and wherein the spring mechanism further comprises first and second pulleys mounted together on a common axis and mounted on the leg bracket, a first cable comprising first and second first cable ends coupled to the spring and the first pulley, respectively, and a second cable comprising first and second cable ends coupled to the second pulley and the leg support, respectively, such that at least a portion of a force from the spring is applied to the leg bracket in the second direction to generate the offset force.

2. The system of claim 1, wherein the spring mechanism is configured to provide a force profile that varies the offset force only in the second direction based on an angle of bending of the one or more joints of the leg support.

3. The system of claim 1, wherein the leg support comprises a leg strap for securing the leg bracket to the upper leg.

4. The system of claim 1, wherein at least one of the first and second pulleys has an asymmetric shape to modify the portion of the force of the spring applied to the leg bracket based on an angle of bending of the hip pivot joint of the leg bracket.

5. The system of claim 1, wherein, in an upright rest position, the spring mechanism applies no support forces to the user's upper leg, and in response to an angle of bend of the upper leg relative to the user's abdomen, a restoring moment is applied that increases to at least partially offset the gravitational force acting on the user's leg.

6. The system of claim 1, wherein the spring mechanism is configured such that, as the user initially bends at the hip, the restoring moment applied by the spring mechanism increases, and, as the user rotates the hip further, a relatively consistent restoring moment is applied.

7. The system of claim 1, wherein the spring mechanism is configured such that, in a dwell region, no restoring moment is applied to the upper leg within a predetermined initial range of motion of the leg.

8. A system for supporting a leg of a user, comprising:
a harness comprising a frame including an attachment band configured to be worn on or around a waist or hips of a user;
a hip strut comprising a first end fixedly coupled relative to the frame such that a second end is configured to be disposed adjacent the user's hip or thigh;
a leg support comprising a leg bracket pivotally coupled to the second end of the hip strut such that the leg bracket is pivotable about a hip pivot joint in a first direction to accommodate bending of the user's upper leg relative to the user's hip while following the bending; and
one or more compensation elements mounted on the leg bracket that applies an offset force that generates a restoring moment around the hip pivot joint only in a second direction opposite to the first direction to at least partially offset a gravitational force acting on the user's body to return the user towards the upright position, wherein the one or more compensation elements comprise a spring mounted on the leg bracket, and wherein the one or more compensation elements further comprise first and second pulleys mounted together on a common axis and mounted on the leg bracket, a first cable comprising first and second first cable ends coupled to the spring and the first pulley, respectively, and a second cable comprising first and second cable ends coupled to the second pulley and the second end of the hip strut, respectively, such that at least a portion of a force from the spring is applied to the leg bracket in the second direction to generate the offset force.

9. The system of claim 8, wherein the leg support further comprises one or more leg straps for securing the leg bracket to the user's upper leg.

10. The system of claim 8, wherein at least one of the first and second pulleys has an asymmetric shape to modify the portion of the force from the spring applied to the leg bracket based on the angle of bending of the hip pivot joint of the leg bracket.

11. The system of claim 8, wherein the hip strut comprises an elastic element configured to provide an axial separating force between the frame and the leg support.

12. The system of claim 8, wherein the leg bracket pivotally coupled to the second end of the hip strut comprises a first leg bracket, the leg support further comprising a first leg strap for securing the first leg bracket to the user's upper leg, the system further comprising:
a second leg bracket pivotally coupled to a second end of the first leg bracket at a knee pivot joint and a second leg strap for securing the first leg bracket to a user's calf such that the second leg bracket is pivotable about the knee pivot joint to accommodate bending of the user's knee while following the bending; and
one or more compensation elements mounted on the second leg bracket to at least partially offset a gravitational force acting on the user's body as the user bends the user's knee and the second leg bracket follow the bending of the user's knee.

13. The system of claim 8, wherein the hip strut comprises an axial elastic element to provide an axial separating force between the first end of the hip strut and the leg bracket.

14. The system of claim 8, wherein the hip strut and leg support comprise a first hip strut and leg support for supporting a first upper leg of the user, the system further comprising:
a second hip strut comprising a first end fixedly coupled relative to the frame such that a second end is configured to be disposed adjacent the user's hip or thigh;
a second leg support comprising a leg bracket pivotally coupled to the second end of the hip strut such that the leg bracket is pivotable about a hip pivot joint in a first direction to accommodate bending of a second upper leg of the user relative to the user's hip while following the bending; and
one or more compensation elements mounted on the leg bracket that applies an offset force that generates a restoring moment around the hip pivot joint only in the second direction to at least partially offset a gravitational force acting on the user's body to return the user towards the upright position.

15. The system of claim 8, wherein the spring is configured to provide a force profile that varies the offset force only in the second direction based on an angle of bending of the one or more joints of the leg support.

16. A system for supporting a leg of a user, comprising:
a harness comprising a frame including an attachment band configured to be worn on or around a waist or hips of a user;
a hip strut comprising a first end fixedly coupled to the frame such that a second end is configured to be disposed adjacent the user's hip or thigh;
a first leg support comprising a first leg bracket pivotally coupled to the second end of the hip strut at a hip pivot joint and a first leg strap for securing the first leg bracket to a user's thigh such that the first leg bracket is pivotable in a first direction about the hip pivot joint as the user crouches or leans forward from an upright position;
a lower leg strut comprising a first end coupled to the first leg bracket and a second end configured to be disposed adjacent the user's thigh or knee;
a second leg support comprising a second leg bracket pivotally coupled to the second end of the lower leg strut at a knee pivot joint and a second leg strap for securing the first leg bracket to a user's calf such that the second leg bracket is pivotable about the knee pivot joint to accommodate bending of the user's knee while following the bending; and
one or more compensation elements mounted on the first and second leg brackets to at least partially offset a gravitational force acting on the user's body as the user bends and the first and second leg brackets follow the bending of the user's upper leg and the user's knee, wherein the one or more compensation elements on the first leg bracket are configured to apply an offset force to the first leg bracket only in a second direction opposite to the first direction to at least partially offset a gravitational force acting on the body and return the user towards the upright position, wherein the one or more compensation elements comprise a spring mounted on the first leg bracket, and wherein the one or more compensation elements further comprise first and second pulleys mounted together on a common axis and mounted on the first leg bracket, a first cable comprising first and second first cable ends coupled to the spring and the first pulley, respectively, and a second cable comprising a first and second cable ends coupled to the second pulley and the second end of the hip strut, respectively, such that at least a portion of a force from the spring is applied to the first leg bracket in the second direction to generate the offset force.

17. The system of claim 16, further comprising a termination element extending from the second leg support.

18. The system of claim 17, wherein the termination element comprises one or more of a roller, pad, or foot configured to transfer weight of the user's body and any equipment or cargo carried by the user to the ground.

19. The system of claim 16, further comprising a hip cassette on the first leg bracket containing the spring, and a knee cassette on the second leg bracket comprising a resilient member configured to at least partially offset a gravitational force acting on the user's leg due to bending at the knee independent of the first cassette.

* * * * *